(12) United States Patent
Hiltawski et al.

(10) Patent No.: US 7,426,024 B2
(45) Date of Patent: Sep. 16, 2008

(54) SYSTEM FOR INSPECTING A DISK-SHAPED OBJECT

(75) Inventors: Knut Hiltawski, deceased, late of Saalfeld (DE); by Magdalena I. Hiltawski, legal representative, Saafeld (DE); by Frank A. Hiltawski, legal representative, Saafeld (DE); René Schenck, Jena (DE)

(73) Assignee: Vistec Semiconductor Systems Jena GmbH, Jena (DE)

( * ) Notice: Subject to any disclaimer, the term of this patent is extended or adjusted under 35 U.S.C. 154(b) by 357 days.

(21) Appl. No.: 11/317,371

(22) Filed: Dec. 22, 2005

(65) Prior Publication Data
US 2007/0186699 A1  Aug. 16, 2007

(30) Foreign Application Priority Data
Dec. 24, 2004  (DE) .................. 10 2004 062 592

(51) Int. Cl.
*G01N 21/00* (2006.01)

(52) U.S. Cl. ................... 356/237.5; 356/237.4

(58) Field of Classification Search ............ 250/559.04, 250/559.08, 559.4–559.46; 382/144–145; 356/237.1–237.5, 239.2–239.8
See application file for complete search history.

(56) References Cited

U.S. PATENT DOCUMENTS

| 5,814,116 | A | 9/1998 | Schneider et al. |
| 7,138,629 | B2 * | 11/2006 | Noji et al. .................. 250/311 |
| 7,265,823 | B2 * | 9/2007 | Kreh et al. ................ 356/237.4 |
| 2002/0009658 | A1 * | 1/2002 | Sato et al. .................. 430/30 |

FOREIGN PATENT DOCUMENTS

| DE | 43 10 149 C2 | 3/1993 |
| DE | 195 38 040 C2 | 10/1996 |
| DE | 103 51 848.7 | 9/2005 |
| EP | 0 335 752 | 10/1989 |

* cited by examiner

*Primary Examiner*—Gregory J Toatley, Jr.
*Assistant Examiner*—Tri T Ton
(74) *Attorney, Agent, or Firm*—Houston Eliseeva LLP

(57) ABSTRACT

A system for inspecting a disc-shaped substrate 5 is disclosed. The system 100 is surrounded by a housing. A table 2 that is movable in at least an X-direction and a Y-direction and is borne by a mounting plate 22 is provided within the housing 50. The mounting plate 22 is vibration isolated in comparison to the housing 50. Equally, an exhaust unit 40 is provided beneath the mounting plate 22 and arranged at a distance from it. The exhaust unit 40 possesses an opening 36 for air entry. The opening 36 for air entry is provided in the exhaust unit between an end of the mounting plate 22 and a wall of the housing 50.

7 Claims, 4 Drawing Sheets

SYSTEM FOR INSPECTING A DISK-SHAPED OBJECT

RELATED APPLICATIONS

This application claims priority to German patent application number DE 10 2004 062 592.1, filed Dec. 24, 2004, which is incorporated herein by reference in its entirety.

FIELD OF INVENTION

The invention relates to a system for inspecting a disc-shaped substrate. In particular, the invention relates to the system for inspecting at least one disc-shaped substrate, whereby the system consists of a housing formed by several walls. Furthermore, the system comprises at least one optical element that is connected with a camera for imaging at least a partial region of a disc-shaped substrate. A mounting plate is provided, which bears a table that is movable in at least an X-direction and a Y-direction. The disc-shaped substrate is placed on the table. The mounting plate is vibration isolated in comparison to the housing.

BACKGROUND OF THE INVENTION

German published application DE 103 51 848.7 discloses a system for detecting macrodefects. The system is surrounded by a housing and subdivided into a first section, a second section, and a third section. In the second section, a table is provided that is movable in at least an X-direction and a Y-direction, onto which a wafer or a disc-shaped substrate, respectively, may be placed. An aspiration device that directs the aspirated air via an air guide is located in the first section, whereby the air guide comprises several air baffles so that an air stream is directed in parallel over the wafer.

DE 43 10 149 C2 discloses a device for handling disc-shaped objects at a working level of an on-site clean room. Furthermore, cartridge receptacles are provided, whose height may be adjusted in relation to the working level. Workstations for processing or inspection purposes are located at the working level. The working level is arranged above an intermediate bottom, which divides the clean room into two partial rooms stacked one on top of the other, in which an air stream component of an air stream is directed from the partial room above the intermediate bottom into the partial room below the intermediate bottom that contains the drive components. The air stream serves to ensure that none of the abraded particles produced by the drive elements reach the workstations in the working level. The air preparation apparatus comprises a housing, and its air vent is divided by circle sector-shaped windows with air baffles. Nothing is mentioned about the particular direction, routing, and/or guides for the air stream within the housing.

German patent DE 195 38 040 C2 discloses a device for generating a clean, turbulent air stream to supply on-site clean rooms. The on-site clean room is surrounded by a housing. The housing possesses an air supply on a side wall. A centrifugal fan is provided behind the air supply, by which the air reaches the interior of the device. An air outlet is provided on the wall that is located opposite the wall with the air supply. The distribution of the air stream in the interior of the on-site clean room is neither mentioned nor considered.

European patent EP 0 335 752 discloses a system for semiconductor production under clean-room conditions. The system comprises a building surrounded by walls, whereby clean-room conditions pertain in a part of the building. The air is fed into the clean room via filters. Holes in the floor of the clean room direct the clean air, for example, to another part of the facility. Nothing is disclosed about how the air stream is routed or directed.

SUMMARY OF THE INVENTION

The object underlying the invention is to create an air stream within a device, without vibrations being transmitted to optical and/or mechanical components of the system.

This object is solved by a system for inspecting a disc-shaped substrate, whereby the system is surrounded by a housing formed by several walls. An optical element and at least one camera are provided for imaging at least a partial region of the disc-shaped object. A mounting plate bears at least one table that is movable in an X-direction and a Y-direction, on which the disc-shaped substrate is placed. The mounting plate is vibration isolated with regard to the housing. An exhaust unit is arranged at a distance below the mounting plate, whereby the exhaust unit is implemented with an opening for air entry, which essentially exhibits a width that corresponds to the distance from the mounting plate to one wall of the housing.

It is particularly advantageous when the system for inspecting a disc-shaped substrate is surrounded by a housing formed out of several walls. Furthermore, an optical element and at least one camera for imaging at least a partial region of the disc-shaped object is provided in the housing. A mounting plate bears at least one table that is movable in an X-direction and a Y-direction, on which the disc-shaped substrate is placed. The mounting plate is vibration isolated with regard to the housing. An exhaust unit is arranged at a distance below the mounting plate, whereby the exhaust unit is implemented with an air inlet opening, which essentially exhibits a width that corresponds to the distance from the mounting plate to one wall of the housing.

The housing is also provided with an air supply unit above the disc-shaped object. The supply unit directs air into the housing.

The exhaust device comprises an upper wall in which the air inlet opening is formed. A lower wall that is located opposite the upper wall bears at least one fan that draws off the air from the exhaust unit. The minimum of one fan in the lower wall is not arranged directly opposite the air inlet opening in the upper wall.

Spatially, the table is arranged midway between the air supply unit and the opening for the exhaust unit, such that the air stream is directed in parallel over the disc-shaped object. The disc-shaped object may be a wafer, a flat-panel display, or a mask.

The transport capacity of the exhaust unit is calibrated such that it does not exceed the transport capacity of the supply unit. Furthermore, the housing may be borne by several different profiles, whereby at least one side wall of the exhaust unit is formed by one of these profiles. It may be additionally advantageous when all of the side walls of the exhaust unit are formed by profiles.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

The subject of the invention is schematically represented in the diagram and is described below based on the figures. They show.

DETAILED DESCRIPTION OF THE PREFERRED EMBODIMENTS

Figure 1:
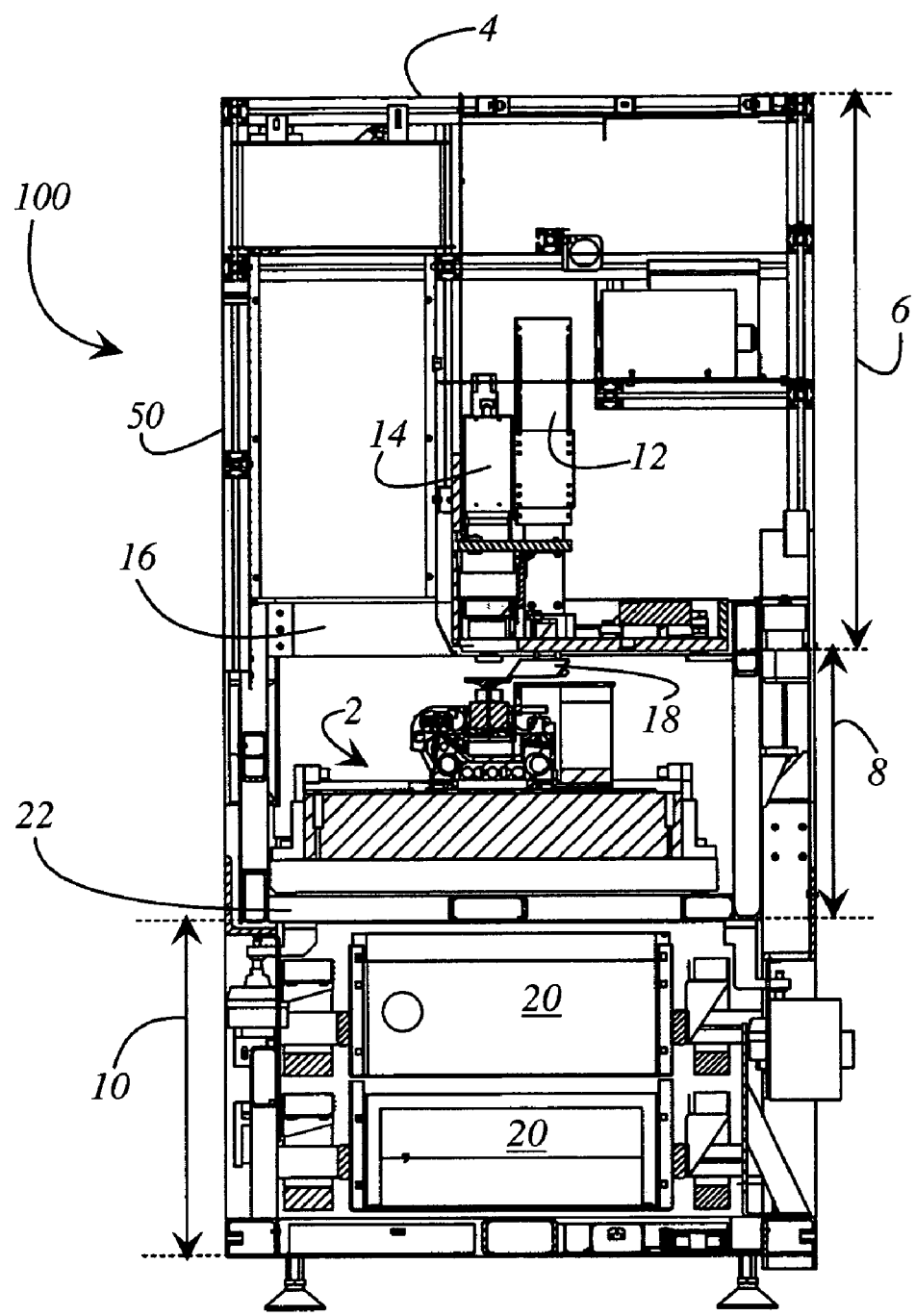
FIG. 1 a schematic representation of the construction of the entire system for inspecting disc-shaped objects and/or the detection of macrodefects.

FIG. 1 shows a representation of the arrangement of the table 2 in the overall system 100 for inspecting wafers or disc-shaped substrates, respectively. The system 100 is surrounded by a housing 50 and is subdivided in the present embodiment into a first section 6, a second section 8, and a third section 10. The housing 50 is sealed by walls (not represented) at all external surfaces, so that specific environmental or clean-room conditions, respectively, are present in the interior of the housing 50. Several illumination devices 12 and at least one detection device 14 are essentially accommodated in the first section 6 of the housing 50. The detection unit 14 is generally a camera or a CCD camera. The first section 6 is separated from the second section 8 by a separation plate 16. The light from the illumination devices 12 is directed via optical devices 18 through the separation plate 16 onto the surface of the wafer to be inspected. The second section 8 is provided with a table 2 that is movable in at least an X-direction and a Y-direction. The table 2 is mounted on a mounting plate 22 that separates the second section 8 from the third section 10. The third section 10 comprises several control units 20 or computers that are responsible for the control and regulation of the system 100 and the individual components of the system 100. In addition, data is acquired and analyzed here.

Figure 2:
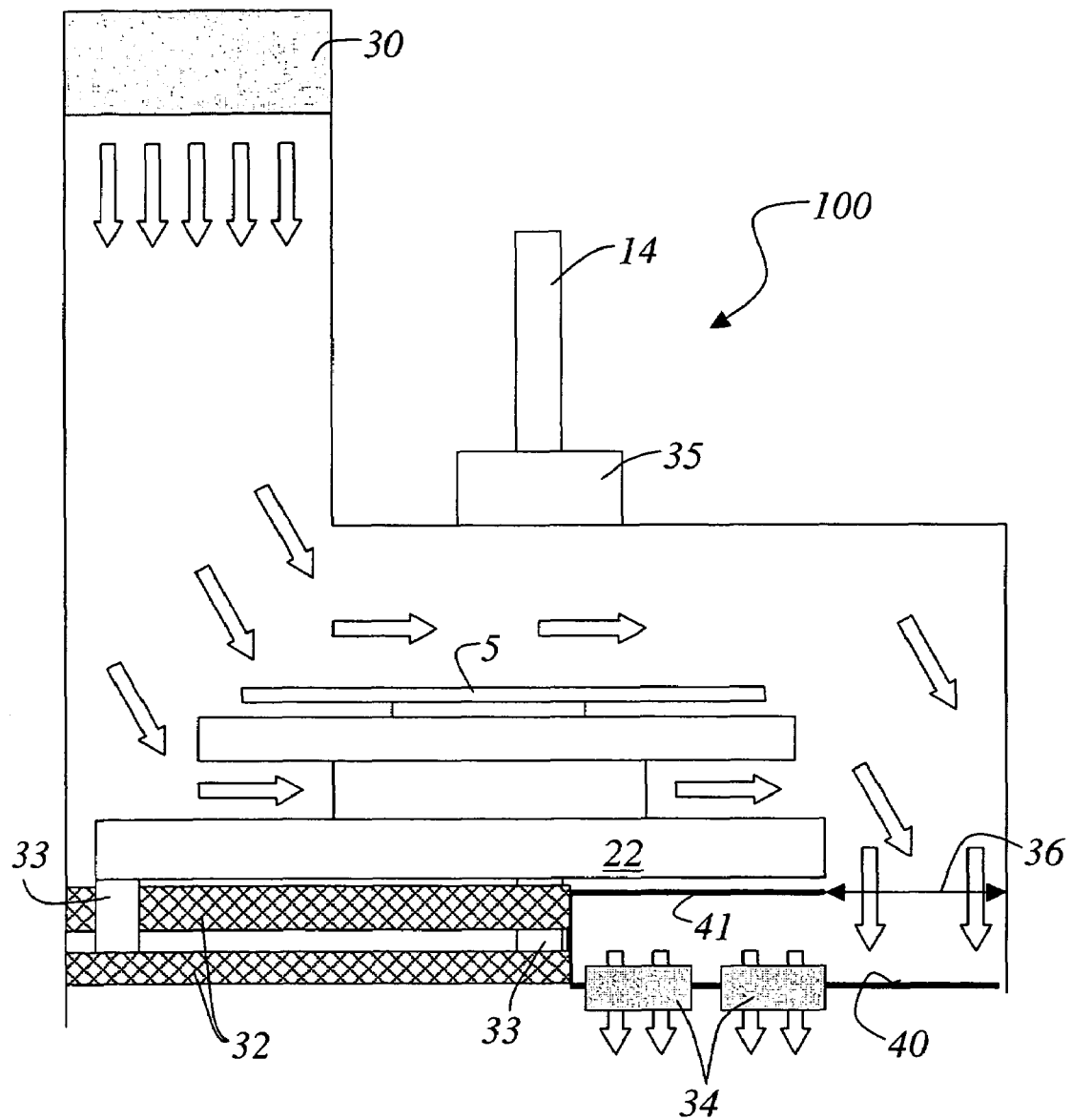
FIG. 2 a schematic representation of the air stream with in the housing of the air supply unit up to the exhaust unit.

FIG. 2 shows a schematic arrangement of a supply unit 30 and an exhaust unit 40 within the system 100 for testing and inspecting disc-shaped substrates. The table 2 that is movable in at least an X-direction and a Y-direction is attached to the mounting plate 22. The walls of the housing 50 arc borne by a rack 32. The rack 37 also bears the mounting plate 22; the mounting plate 22 is separated from the rack 32 1w a vibration isolator. The exhaust unit 40 is arranged beneath the mounting plate 22. whereby the exhaust unit 40 is at a distance from the mounting plate 22. At least one Pin 34 is provided in the exhaust unit 40. which draws and exhausts the air from the interior of the housing 50. Because of the distance between the exhaust unit 40 and the mounting plate 22. no vibrations from the fan 34 are transmitted either to the mounting plate 22 or to the table 2 that is movable in an X-direction and a Y-direction The disc-shaped substrate 5 that is intended for inspecting is placed on the table. The housing is provided with at least one optical element 35 that images at least a partial region of the disc-shaped substrate so that a camera 14 may take an image of this partial region of the disc-shaped substrate 5.The air supply unit is arranged above the surface of the disc-shaped substrate 5. The air supply unit is provided on one side of the housing and the air exhaust unit 40 is provided on the opposite side of the housing 50. The air exhaust unit 40 is implemented with an opening 36 through which the air to be exhausted reaches the exhaust unit 40.. The mounting plate 22 in the interior of the housing 50 is at a distance from a side wall of the housing 50. The opening 36 in the exhaust unit 40 is implemented such that in its width it corresponds approximately to the distance between the mounting plate 22 and the wall of the housing 50. The exhaust unit 40 is implemented with an upper wall 41 and a lower wall 42. The opening 36 through which air enters the exhaust unit 40 is implemented in the upper wall 41. Spatially. the table 2 is arranged midway between the air supply unit 30 and the opening for the air exhaust unit 40. such that an air stream (shown as arrows in FIG. 2) is directed in parallel over the disc-shaped object 5. The transport capacity of the exhaust unit 40 is calibrated such that it does not exceed the transport capacity of the supply unit 30. As a result. a slight positive pressure is built up within the housing in comparison to the pressure outside the housing 50.

Figure 3:
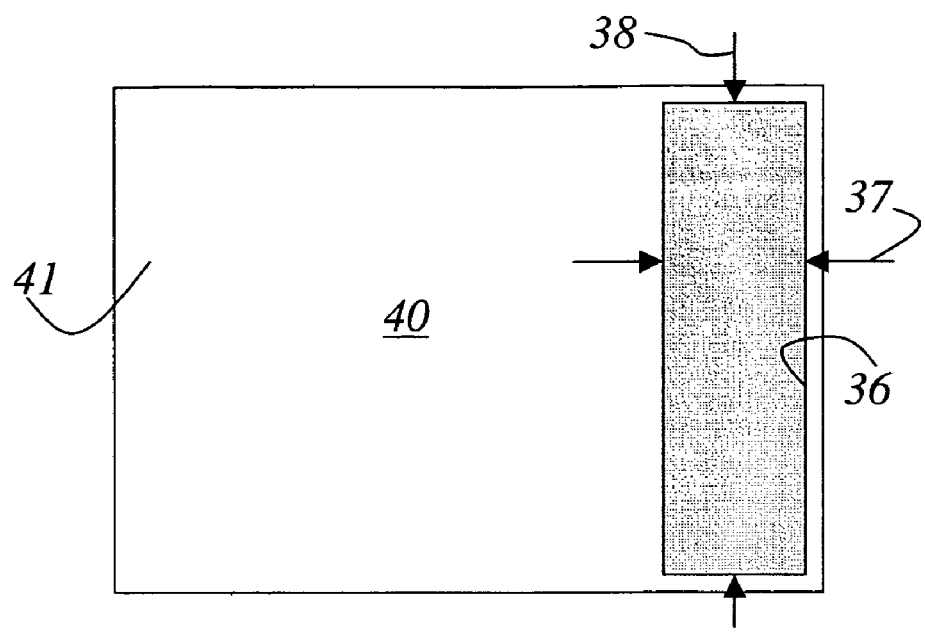
FIG. 3 a perspective view of the exhaust unit.

FIG. 3 shows a top view of an exhaust unit 40. The opening 36 through which air enters is implemented in the upper wall 41 of the exhaust unit 40. In the embodiment represented here, the opening 36 is rectangular, which should not, however, be interpreted as a limitation. It will be clear to any person skilled in the art that any form may be used for the opening 36. The opening 36 as aforementioned, has a width 37 that essentially corresponds to the distance between the mounting plate 22 and a wall of the housing 50. The length 38 of the opening 36 extends essentially over the entire width of the exhaust unit 40.

Figure 4:
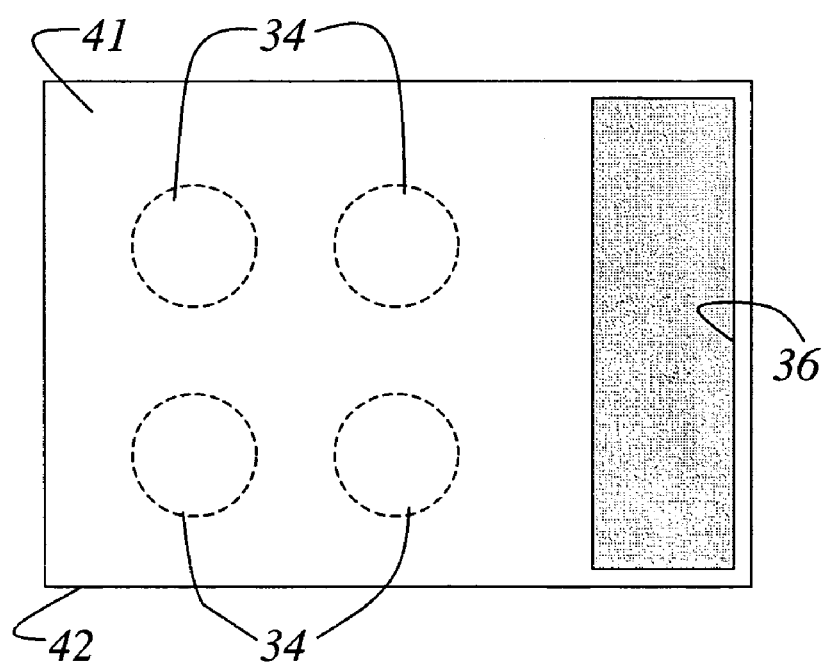
FIG. 4 a schematic top view of the exhaust unit, whereby the upper wall is represented, and the lower wall is represented in broken line.

FIG. 4 shows atop view of the exhaust unit 40. whereby the lower wall is represented as well. The arrangement of the fans 34 in the lower wall 42 of the exhaust unit 40 is indicated by a broken line. The fans 34 are arranged in the lower wall 42 such that they are nor directly opposite the opening 36 through which air enters in the upper wall 41 of the exhaust unit. The number of fans 34 in the lower wall 42 of the exhaust unit 40 depends on the quantity of air to be moved. It will be obvious to a person skilled in the art that there is a multiplicity of design possibilities with regard to the number of fans and the arrangement of the fans 34.

Figure 5:
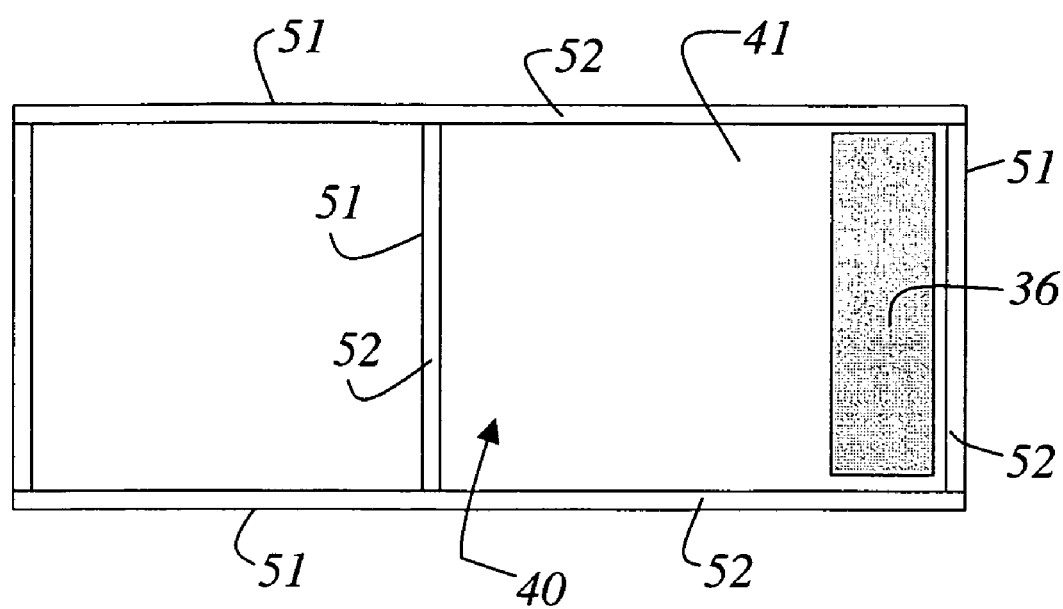
FIG. 5 a schematic view of the exhaust unit with respect to its arrangement in the housing.

FIG. 5 shows a schematic representation of the arrangement of the exhaust unit 40 within the housing 50. The housing 50 of the system is borne by several profiles 51. The exhaust unit 41 is dimensioned within the housing such that the profiles 51 form the side walls 52 of the housing of the exhaust unit. This greatly facilitates assembly and mounting of the entire system 100. The upper wall 41 of the exhaust unit 40 and the lower wall 42 of the exhaust unit 40 must merely be attached onto or to the profiles 51. The upper wall 41 and the lower wall 42 together with the profiles 51 thus form the housing for the exhaust unit 40.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for inspecting a disc-shaped object,
    whereby the system is surrounded by a housing formed of several walls, wherein an optical element and at least one camera for imaging at least a partial region of the disc-shaped object are provided, wherein an air supply unit is provided above the disc-shaped object that directs the air into the housing, wherein a mounting plate bears a table that is movable in at least an X-direction and a Y-direction on which the disc-shaped object is placed, whereby the mounting plate is vibration isolated in comparison to the housing, wherein an exhaust unit is arranged beneath the mounting plate at a distance, wherein an air inlet opening is implemented in an upper wall of the exhaust unit having a width that essentially corresponds to the distance between the mounting plate and a wall of the housing, wherein the exhaust unit has a lower wall opposite to the upper wall, the lower wall bears at least one fan that draws the air out of the exhaust unit, and wherein the transport capacity of the exhaust unit is calibrated such that it does not exceed the transport capacity of the supply unit.

2. The system according to claim 1, wherein the minimum of one fan is arranged in the lower wall not directly opposite the air inlet opening in the upper wall.

3. The system according to claim 1, wherein the table is arranged spatially midway between the air supply unit and the opening of the exhaust unit such that an air stream is directed in parallel over the disc-shaped object.

4. The system according to claim 1, wherein the disc-shaped object is a wafer or a flat panel display, or a mask.

5. The system according to claim 1, wherein the housing is borne by several profiles, and wherein at least one side wall of the exhaust unit is formed by one of the profiles.

6. The system according to claim 5, wherein all of the side walls of the exhaust unit are formed by the profiles.

7. The system according to claim 1, wherein the optical element is a lens or an objective.

* * * * *